United States Patent [19]

Ezaki et al.

[11] Patent Number: 4,654,211

[45] Date of Patent: Mar. 31, 1987

[54] NEW COMPOUND, FR-900451, PRODUCTION AND USE THEREOF

[75] Inventors: Masami Ezaki, Osaka; Seiji Hashimoto, Deguchicho; Tadaaki Komori, Takatsuki; Kazuyoshi Umehara, Asahigaokacho; Masanobu Kohsaka, Akasakadai, all of Japan

[73] Assignee: Fujisawa Pharmaceutical Co., Ltd., Osaka, Japan

[21] Appl. No.: 677,013

[22] Filed: Nov. 30, 1984

[30] Foreign Application Priority Data

Dec. 5, 1983 [GB] United Kingdom ................. 8332390

[51] Int. Cl.$^4$ ........................ A61K 35/00; C12P 1/06; C12N 1/20; C12R 1/465
[52] U.S. Cl. ................................... 424/116; 435/169; 435/253; 435/886
[58] Field of Search ................ 424/116, 118; 435/253, 435/169

[56] References Cited

U.S. PATENT DOCUMENTS 4,313,935  2/1982  Komori et al. ...................... 435/169

OTHER PUBLICATIONS

American Type Culture Collection Catalogue of Strains I, 15th Ed., p. 214, 1982.

*Primary Examiner*—Alvin E. Tanenholtz
*Attorney, Agent, or Firm*—Oblon, Fisher, Spivak, McClelland & Maier

[57] ABSTRACT

Antibiotic FR-900451 is produced by *Streptomyces griseorubiginosus* No. 43708 (FERM BP-699).

4 Claims, No Drawings

NEW COMPOUND, FR-900451, PRODUCTION AND USE THEREOF

This invention relates to a new compound, FR-900451. More particularly, it relates to a new compound, FR-900451 and pharmaceutically acceptable salt thereof which have a strong antimicrobial activity against pathogenic bacteria, especially pathogenic Gram positive bacteria, to a process for the preparation thereof and to pharmaceutical composition thereof.

Accordingly, one object of this invention is to provide a new compound, FR-900451 and pharmaceutically acceptable salt thereof which have antimicrobial activity, and are useful for the treatment of infectious diseases in human beings and animals.

Another object of this invention is to provide a process for preparing FR-900451 by culturing a FR-900451 producing strain belonging to the genus Streptomyces in a nutrient medium.

A further object of this invention is to provide a pharmaceutical composition comprising FR-900451 or pharmaceutically acceptable salt thereof as an active ingredient.

According to this invention, the FR-900451 can be prepared by culturing a FR-900451 producing strain belonging to the genus Streptomyces such as *Streptomyces griseorubiginosus* No. 43708 and the like in a nutrient medium.

Particulars of microorganisms used for producing FR-900451 and production thereof will be explained in the followings.

MICROORGANISM

The microorganism which can be used for the production of FR-900451 is a FR-900451 producing strain belonging to the genus Streptomyces, among which *Streptomyces griseorubiginosus* No. 43708 has been newly isolated from a soil sample collected in Akashi City, Japan.

A lyophilized sample of the newly isolated microorganism has been deposited with an international depositary authority on Budapest Treaty, Fermentation Research institute, Agency of Industrial Science and Technology, Yatabe-cho higashi No. 1-1-3, Tsukuba-gun, Ibaraki-ken, Japan, under the number FERM BP-669 on Nov. 24, 1983.

It is to be understood that the production of the new compound, FR-900451 is not limited to the use of the particular organism described herein, which is given for illustrative purpose only. This invention also includes the use of any mutants which are capable of producing the FR-900451 including natural mutants as well as artificial mutants which can be produced from the described organism by conventional means, such as X-rays, ultra-violet radiation, treatment with N-methyl-N'-nitro-N-nitrosoguanidine, 2-aminopurine and the like.

*Streptomyces griseorubiginosus* No. 43708 has the following morphological, cultural, biological and physiological characteristics.

1. Morphological Characteristics

The methods described by Shirling and Gottlieb [Vide.International Journal of Systematic Bacteriology 16, 313-340(1966)] were employed principally for this taxonomic study. Morphological observations were made with light and electron microscopes on cultures grown at 30° C. for 14 days on yeast-malt extract agar, oatmeal agar or inorganic salts-starch agar. The mature spores occurred in chains of more than 30 spores forming Rectiflexibiles. The spores were cylindrical and 0.5–0.7×1.3–1.5 μm in size by electron microscopic observations. Spore surfaces were smooth or warty.

2. Cultural Characteristics

Cultural characteristics were observed on ten kinds of media described by Shirling and Gottlieb [Vide. the same literature as mentioned above)] and Waksman [Vide. The Actinomycetes Vol. 2 (1961)]. The incubation was made at 30° C. for 14 days. The color names used in this study were based on Color Standard (Nihon Shikisai Co., Ltd.). Colonies belonged to the gray color series when grown on oatmeal agar, yeast-malt extract agar and inorganic salts-starch agar. Soluble pigment was produced in yeast-malt extract agar and others. Results were shown in Table 1.

TABLE 1

Cultural characteristics of strain No. 43708 and *Streptomyces griseorubiginosus* IFO 13047, *Streptomyces phaeopurpureus* IFO 12899 and *Streptomyces phaeoviridis* IFO 12900.

| Medium | | No. 43708 | IFO 13047 | IFO 12899 | IFO 12900 |
|---|---|---|---|---|---|
| Oatmeal agar | G | poor | poor | moderate | poor |
| | A | grayish white | grayish white | grayish white | light gray |
| | R | pale pink | pale pink | pale cinnamon pink orange | colorless |
| | S | pale pink | pale pink | pale yellow | none |
| Yeast-malt extract agar | G | abundant | abundant | abundant | moderate |
| | A | light gray | light gray | light gray | light gray |
| | R | brown | brown | pale reddish brown | light brown |
| | S | dull reddish orange | dull reddish orange | brown | none |
| Inorganic salts-starch agar | G | abundant | moderate | moderate | moderate |
| | A | light gray | gray | light gray | white |
| | R | pale yellow orange | pale yellowish brown | pale yellowish brown | pale yellow |
| | S | pale yellow | pale yellow | none | none |
| Glycerin-asparagine agar | G | abundant | abundant | abundant | moderate |
| | A | light gray | gray | light gray | gray |
| | R | dull gray | dull reddish orange | reddish orange | yellowish brown |
| | S | brown | pale yellow orange | reddish orange | none |
| Sucrose-nitrate agar | G | abundant | abundant | abundant | moderate |
| | A | none | none | none | none |

TABLE 1-continued

Cultural characteristics of strain No. 43708 and Streptomyces griseorubiginosus IFO 13047, Streptomyces phaeopurpureus IFO 12899 and Streptomyces phaeoviridis IFO 12900.

| Medium | | No. 43708 | IFO 13047 | IFO 12899 | IFO 12900 |
|---|---|---|---|---|---|
| Nutrient agar | R | brown | brown | reddish orange | colorless |
| | S | pale orange | pale orange | none | none |
| | G | moderate | moderate | moderate | poor |
| | A | none | none | none | grayish white |
| Potato-dextrose agar | R | colorless | colorless | pale yellow brown | pale yellow |
| | S | pale yellow | pale yellow | none | none |
| | G | abundant | abundant | moderate | moderate |
| | A | light gray | light gray | light gray to pale yellow orange | pale yellow orange |
| Tyrosine agar | R | dark reddish brown | dark reddish brown | brown | pale yellow brown |
| | S | none | none | brown | pale yellow |
| | G | abundant | abundant | abundant | abundant |
| | A | pale cinnamon pink | pale cinnamon pink | gray | gray |
| Peptone-yeast extract-iron agar | R | black | black | black | dark brown |
| | S | dark brown | dark brown to black | black | dark brown |
| | G | moderate | moderate | moderate | moderate |
| | A | none | none | none | none |
| | R | colorless | colorless | colorless | colorless |
| | S | black | black | black | black |

Abbreviation:
G = growth
A = aerial mass color
R = reverse side color
S = soluble pigment The cell wall analysis was performed by the methods of Becker et al. [Vide. Applied Microbiology 12, 421–423(1964)] and Yamaguchi [Vide. Journal of Bacteriology 89, 444–453(1964)]. Analysis of whole cell hydrolysates of strain No. 43708 showed that it contained LL-diaminopimeric acid. Accordingly, the cell wall of this strain was believed to be of type I.

3. Biological and physiological properties

Physiological properties of strain No. 43708 were shown in Table 2. Temperature range and optimum temperature for growth were determined on yeast-malt extract agar using a temperature gradient incubator (Toyo Kagaku Sangyo Co., Ltd.). Temperature range for growth was from 17° C. to 41° C. with optimum from 29° C. to 31° C. Starch hydrolysis, milk Peptonization, melanin production, gelatin liquefaction and $H_2S$ production were positive.

TABLE 2

Physiological properties of strain No. 43708 and Streptomyces griseorubiginosus IFO 13047

| | No. 43708 | IFO 13047 |
|---|---|---|
| Temperature range for growth | 17° C.–41° C. | 17° C.–41° C. |
| Optimum temperature | 29° C.–31° C. | 29° C. |
| Nitrate reduction | negative | negative |
| Starch hydrolysis | positive | positive |
| Milk coagulation | negative | negative |
| Milk peptonization | positive | positive |
| Melanin production | positive | positive |
| Gelatin liquefaction | positive | positive |
| $H_2S$ production | positive | positive |
| Urease activity | negative | negative |
| NaCl tolerance (%) | <7% | <10% |

Utilization of carbon sources was examined according to the methods of Pridham and Gottlieb [Vide. Journal of Bacteriology 56, 107–114 (1948)]. Almost all carbon sources were utilized except cellulose, chitin and sodium acetate. Summarized carbon sources utilization of this strain is shown in Table 3.

TABLE 3

Carbon sources utilization of strain No. 43708 and Streptomyces griseorubiginosus IFO 13047.

| | No. 43708 | IFO 13047 |
|---|---|---|
| D-Glucose | + | + |
| Sucrose | + | + |
| Glycerin | + | + |
| D-Xylose | + | + |
| D-Fructose | + | + |
| Lactose | + | + |
| Maltose | + | + |
| Rhamnose | + | + |
| Raffinose | ± | + |
| D-Galactose | + | + |
| L-Arabinose | + | + |
| D-Mannose | + | + |
| D-Trehalose | ± | ± |
| Inositol | + | + |
| Mannitol | + | + |
| Inulin | ± | + |
| Cellulose | − | − |
| Salicin | + | + |
| Chitin | − | − |
| Sodium citrate | + | + |
| Sodium succinate | + | + |
| Sodium acetate | − | − |

Symbols:
+ = utilization
± = doubtful utilization
− = no utilization

Microscopic studies and cell wall composition analysis of this strain indicate that strain No. 43708 belongs to the genus Streptomyces Waksman and Henrici 1943. Accordingly, a comparison of this strain was made with the published descriptions [International Journal of Systematic Bacteriology 18, 69–189, 279–392(1968) and 19, 391–512(1969), and Bergey's Manual of Determinative Bacteriology 8th Edition(1974)] of various Streptomyces species. Strain No. 43708 is considered to resemble Streptomyces griseorubiginosus (Ryabova and Preobrazhenskaya 1957) Pridham, Hesseltine and Benedict 1958, Streptomyces phaeopurpureus Shinobu 1957, Streptomyces phaeoviridis Shinobu 1957. Therefore, cultural characteristics of strain No. 43708 was compared with these three species. As shown in Table 1, strain No. 43708 closely resembled *Streptomyces griseorubiginosus* IFO 13047. Therefore, further detailed comparison was made with strain No. 43708 and *S. griseorubiginosus* IFO 13047. As shown in Table 2 and 3, strain No. 43708 is in good agreement with *Streptomyces griseorubiginosus* IFO 13047 except NaCl tolerance and utilization of raffinose and inulin. These differences do not seem to sufficiently distinguish strain No. 43708 from *S. griseorubiginosus*. Therefore, strain No. 43708 is identified as *Streptomyces griseorubiginosus* No. 43708.

PRODUCTION OF FR-900451

The new compound, FR-900451 can be produced by culturing a FR-900451 producing strain belonging to the genus Streptomyces, such as *Streptomyces griseorubiginosus* No. 43708 in a nutrient medium.

In general, FR-900451 can be produced by culturing a FR-900451 producing strain in a nutrient medium containing assimilable sources of carbon and of nitrogen, preferably under aerobic conditions (e.g. shaking culture, submerged culture, etc.).

The preferred sources of carbon in the nutrient medium are carbohydrates such as glucose, fructose, glycerin and starch. Other sources which may be included are lactose, arabinose, xylose, dextrin, molasses and the like.

The preferred sources of nitrogen are yeast extract, peptone, gluten meal, cottonseed meal, soybean meal, corn steep liquor, dried yeast, etc., as well as inorganic and organic nitrogen compounds such as ammonium salts (e.g. ammonium nitrate, ammonium sulphate, ammonium phosphate, etc.), urea, amino acid and the like.

The carbon and nitrogen sources, though advantageously employed in combination, need not be used in their pure form because less pure materials which contain traces of growth factors and considerable quantities of mineral nutrients, are also suitable for use. When desired, there may be added to medium such mineral salts as calcium carbonate, sodium or potassium phosphate, sodium or potassium iodide, magnesium salt, cobalt chloride and the like. If necessary, especially when the culture medium is foamed remarkably, a defoaming agent such as liquid paraffin, higher alcohol, plant oil, mineral oil and silicones may be added.

As conditions for the production in massive amounts, submerged aerobic cultural condition is preferred for the production of the FR-900451. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of the FR-900451. Accordingly, it is desirable first to produce a vegetative inoculum of the organism by inoculating a relatively small quantity of culture medium with spores or mycelia of the organism and culturing said inoculated medium, and then to transfer the cultured vegetative inoculum aseptically to large tanks. As the medium, in which the vegetative inoculum is produced, there can be used the substantially same as or somewhat different medium from medium utilized for main production of the FR-900451.

Agitation and aeration of the culture mixture may be accomplished in a variety of ways. Agitation may be provided by a propeller or the similar mechanical agitation equipment, by revolving or shaking the fermenter, by various pumping equipment or by the passage of sterile air through the medium. Aeration may be effected by passing sterile air through the fermentation mixture.

The fermentation is usually conducted at a temperature about between 20° C. and 40° C., preferably around 30° C., for a period of 50 hours to 100 hours, which may be varied according to the fermentation conditions and scale.

Thus produced FR-900451 can be recovered from the culture medium by conventional means which are commonly used for the recovery of other fermentation products such as antibiotics.

In general, most of the FR-900451 produced are found in the culture filtrate, and accordingly FR-900451 can be isolated from the filtrate, which is obtained by filtering or centrifuging the broth, by a conventional method such as concentration under reduced pressure, lyophilization, extraction with a conventional solvent, pH adjustment, treatment with a conventional resin (e.g. anion or cation exchange resin, non-ionic adsorption resin), treatment with a conventional adsorbent (e.g. activated charcoal, silicic acid, silica gel, cellulose, alumina), crystallization, recrystallization and the like.

The FR-900451 obtained in its free form may also be converted to its acid addition salts by treating FR-900451 with an inorganic or organic acid such as hydrochloric acid, sulfuric acid, phosphoric acid, acetic acid, p-toluene sulfonic acid and the like.

The phosphoric acid salt of FR-900451 as obtained according to the aforementioned process has the following physical and chemical properties:

(1) Elemental Analysis (%): C44.64; H5.35; N8.73; P4.80.

(2) Molecular weight: 488[FAB mass spectrometry: m/z 489 (M+1)].

(3) Melting point: 205° C. (dec.).

(4) Specific rotation: $[\alpha]_D^{25} = -30.2°$ (c=0.1, H$_2$O).

(5) Ultraviolet absorption spectrum:
$\lambda_{max}^{H2O} = 260$ nm (E$_{1\ cm}^{1\%} = 125$);
$\lambda_{max}^{H2O+HCl} = 260$ nm (E$_{1\ cm}^{1\%} = 127$);
$\lambda_{max}^{H2O+NaOH} = 288$ nm (E$_{1\ cm}^{1\%} = 230$).

(6) Infrared absorption spectrum: $\nu_{max}^{KBr} = 3700-2200$ (broad), 1750–1460 (broad), 1440, 1375, 1280–1220 (broad), 1170–880 (broad), 820, 760–700 (broad) cm$^{-1}$.

(7) Nuclear magnetic resonance absorption spectrum: δppm (D$_2$O+DCl):
1.96 (1H, d.d.d., J=14 Hz, 9 Hz and 7 Hz),
2.15 (1H, d.d.d., J=14 Hz, 9 Hz and 4 Hz),
2.97 (1H, d.d., J=13 Hz and 10 Hz),
3.03 (1H, d.d., J=16 Hz and 3 Hz),
3.21 (1H, d.d., J=13 Hz and 3 Hz),
3.57 (1H, d.d., J=16 Hz and 5 Hz),
4.13 (1H, m),
4.50 (1H, d.d., J=5 Hz and 3 Hz),
4.91 (1H, s),
5.02 (1H, d.d., J=9 Hz and 7 Hz),
5.84 (1H, s),
6.87 (1H, broad s),
6.96 (2H, m),
7.40 (3H, m).

(8) Solubility:
Soluble: Water;
Sparingly soluble: Acetone, ethanol;
Insoluble: Hexane, ethyl acetate, chloroform.

(9) Color reaction:
Positive: Ninhydrin reaction and ferric chloride-patassium ferricyanide reaction;

Negative: Molish's reaction, reaction with Dragendorff reagent or diacetyl reagent.

(10) Property of substance:
Basic substance.

(11) $^{13}$C-Nuclear magnetic resonance absorption spectrum: δ(ppm) (D$_2$O+DCl): 174.0, 173.2, 168.6, 154.2, 152.8, 133.0, 132.9, 130.6, 127.9, 127.6, 127.2, 126.2, 120.3, 116.9, 116.4, 65.2, 64.4, 57.4, 55.0, 50.9, 44.9, 37.9, 30.4.

(12) Thin layer chromatography (silica gel sheet):

| Solvent | Rf value |
| --- | --- |
| A mixture of n-butanol, ethanol, chloroform and 17% aqueous ammonia (4:7:2:7) | 0.54 |

The FR-900451 has a strong antimicrobial activity against pathogenic microorgainsms such as Gram-positive bacteria and Mycobacterium (e.g. Mycobacterium tuberculosis). Accordingly, the FR-900451 and its pharmaceutically acceptable salt are useful as an antimicrobial agent which is used for the treatment of infectious diseases in human beings and animals.

As examples for showing such pharmacological effects of the FR-900451, some pharmacological test data are illustrated in the followings.

Test 1 [Minimum inhibitory concentration (M.I.C.)]

The minimum inhibitory concentrations of the phosphoric acid salt of FR-900451 against various pathogenic microorganisms were determined by a conventional agar dilution method using a serum agar containing 10% of horse serum and 1% of agar (Difco). The results are shown in the following.

| Microorganism | M.I.C (μg/ml) |
| --- | --- |
| Staphylococcus aureus 209P | 0.32 |
| Streptococcus faecalis FP183 | <0.08 |
| Streptococcus pneumoniae FP166 | <0.16 |
| Escherichia coli No. 22 | 25 |
| Proteus vulgaris No. 8 | 25 |
| Pseudomonas aeruginosa | >200 |
| Candida albicans | >200 |

Test 2 [Protecting Effect in Experimental Mice Infections]

(a) Test compound
Phosphoric acid salt of the FR-900451.
(b) Test animal
Male mice of ICR-strain weighing 20 g was used.
Each experimental group consists of 5 animals.
(c) Test method
A prescribed amount of pathogenic bacteria, suspended in 5% aqueous Mucin (0.5 ml), was intraperitoneally injected into the test animals.

Subsequently, the above test compound in water (0.25 ml) was administered to each of the test animals subcutaneously once at 1 hour after the infection of pathogenic bacteria, respectively.

All test animals were observed for survival or death for 1 week. The results are shown in the following table.

TABLE

| Pathogenic bacteria | Inoculated viable cells per mouse | Dosage of the test compound (mg/kg) | Survival (%) |
| --- | --- | --- | --- |
| Staphylococcus aureus No. 47 | 1 × 10$^7$ | 0.3 | 100 |
| Escherichia coli No. 22 | 5 × 10$^2$ | 30 | 100 |
| Proteus vulgaris No. 8 | 1 × 10$^5$ | 30 | 100 |

Acute toxicity of phosphoric acid salt of the FR-900451 (intravenous injection into mice):
>500 mg/kg The object compound, the FR-900451 and its pharmaceutically acceptable salt, can be formulated for administration in any convenient way, analogously with known antibiotics, in admixture with a non-toxic pharmaceutically acceptable carrier.

A pharmaceutically acceptable salt of the FR-900451 may include a salt with an inorganic or organic acid such as hydrochloride, sulfate, citrate, maleate, fumarate, tartarate, p-toluenesulfonate and the like, and further salt with an amino acid such as arginine salt, aspartic acid salt, glutanic acid salt, and the like.

Thus, the antimicrobial composition can be used in the form of pharmaceutical preparation, for example, in solid, semisolid or liquid form, which contains an active object compound in admixture with a pharmaceutical organic or inorganic carrier or excipient suitable for external, enteral or parenteral applications. The active ingredient may be compounded, for example, with usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, karatin, colloidal silica, potato starch, urea and other carriers suitable for use in manufacturing preparations, in solid, semi-solid, or liquid form, and in addition auxiliary, stabilizing, thickening and coloring agents and perfumes. The antimicrobial compositions can also contain preserving or bacteriostatic agents thereby keeping the active ingredient in the desired preparations stable in activity. The active object compound is included in the antimicrobial composition in an amount sufficient to produce the desired therapeutic effect upon the bacterially infected process or condition.

For applying this composition to human, it is preferably to apply in a form of intravenous, intramuscular or oral administration. While the dosage or therapeutically effective amount of the object compound of this invention varies from and also depends upon the age and condition of each individual patient to be treated, a daily dose of about 2–100 mg. of the active ingredient/kg. of a human being or an animal is generally given for treating diseases and an average single dose of about 50 mg., 100 mg., 250 mg. and 500 mg. is generally administered.

The following Examples are given for the purpose of illustrating this invention, but not limited thereto.

EXAMPLE 1

An aqueous medium (160 ml) containing 1% of corn starch, 1% of glycerin, 0.5% of glucose, 1% of cotton seed flour, 0.5% of dried yeast, 0.5% of corn steep liquor (pH 6.5) and 0.2% of calcium carbonate was poured into each of ten 500 ml. Erlenmeyer-flasks and sterilized at 120° C. for 20 minutes. A loopful of slant culture of *Streptomyces griseorubiginosus* No. 43708 was inoculated to each of the medium and cultured on a rotary shaker (7.6 cm throw at 180 rev./minute) at 30° C. for 48 hours. The resultant cultured broth was inoculated to an aqueous medium (150 liters) containing 5% of sucrose, 0.5% of dried yeast, 0.1% of $K_2HPO_4$, 0.1% of $MgSO_4.7H_2O$, 0.1% of NaCl, 0.5% of $CaCO_3$, 0.001% of $FeSO_4.7H_2O$, 0.0004% of $CoCl_2.6H_2O$, 0.01% of NaI, 0.5% of $(NH_4)_2SO_4$ and 0.13% of a defoaming agent in a 200 liter-fermentor which has been sterilized at 120° C. for 20 minutes in advance, and cultured at 30° C. for 90 hours (fermentation conditions: agitation 150 rpm; aeration 150 liters/minute; tank back pressure 1 kg/cm$^2$).

After fermentation was completed, the cultured broth (140 liters) was filtered with the aid of diatomaceous earth (10 kg). The filtrate (120 liters) was adsorbed on a column of non-ionic adsorption resin Diaion HP-20 (trade mark, made by Mitsubishi Chemical Ind.) (40 liters). The column was washed with water (120 liters), and then eluted with 50% methanol-water. This eluate (50 liters) was concentrated in vacuo to 7 liters. The solution was adsorbed on a column of CM-Sephadex C-25 (trade mark, made by Pharmacia AB) ($NH_4^+$). The column was successively washed with water (1.5 liters) and 1M aqueous sodium chloride (1 liter) and then eluted with 2M aqueous sodium chloride (2.75 liters). The active fraction was adsorbed on a 700 ml bed of non-ionic adsorption resin Diaion HP-20. The column was washed with water, eluted with 3 liters of 60% aqueous methanol and then concentrated under reduced pressure to 450 ml. The concentrate was applied to a column of DEAE-Sephadex A-25 ($OH^-$) (trade mark, made by Pharmacia AB) (120 ml). The column was successively washed with water (240 ml) and 0.2M aqueous sodium chloride (200 ml), and eluted with 0.4M aqueous sodium chloride (650 ml). The eluate was diluted with water, and then desalted with CM-Sephadex C-25 ($NH_4^+$) (280 ml). The active fraction containing 1% ammoniac solution was concentrated in vacuo to the smallest possible volume and neutralized by 1N hydrochloric acid. A 2 ml aliquot of the concentrated eluate was applied to a ODS-Q3 gel column (trade mark, made by Fuji Gel Col, Ltd.) (1×21.5 cm), and the column was developed with a mixture of 0.1M phosphate buffer and acetonitrile (90:8, pH 4.8). Fractions of 15 ml were collected. The active solution was desalted using the Diaion HP-20 and lyophilized to give phosphoric acid salt of FR-900451 (3.2 mg) in the form of white powder.

EXAMPLE 2

The required quantities of sterile antibiotic, phosphoric acid salt of the FR-900451 are distributed into vials, thereby containing 500 mg. of the active ingredient. The vials are sealed hermetically to exclude bacteria. Whenever the vials are required for use, 2 ml of sterile distilled water for injection is added to the vial and the vial is subjected to administration.

We claim:

1. A compound FR-900451 and pharmaceutically acceptable salts thereof, having the following characteristics:

(a) is effective in inhibiting the growth of various Gram-positive and Gram-negative bacteria; and as its phosphoric acid salt, (b) has the following elemental analysis (%): C44.64; H5.35; N8.73; P4.80;

(c) has a molecular weight: 488[FAB mass spectrometry: m/z 489 (M+1)];

(d) has a melting point at 205° C. (dec.);

(e) has an optical rotation: $[\alpha]_D^{25} = -30.2°$ (c=0.1, $H_2O$);

(f) has a characteristic ultraviolet absorption spectrum as shown in the following,
$\lambda_{max}^{H2O} = 260$ nm ($E_{1\ cm}^{1\%} = 125$);
$\lambda_{max}^{H2O+HCl} = 260$ nm ($E_{1\ cm}^{1\%} = 127$);
$\lambda_{max}^{H2O+NaOH} = 288$ nm ($E_{1\ cm}^{1\%} = 230$);

(g) has a characteristic infrared absorption spectrum as shown in the following, $\nu_{max}^{KBr} = 3700-2200$ (broad), 1750-1460 (broad), 1440, 1375, 1280-1220 (broad), 1170-880 (broad), 820, 760-700 (broad) cm$^{-1}$;

(h) has a characteristic nuclear magnetic resonance absorption spectrum as shown in the following, δppm ($D_2O+DCl$):
1.96 (1H, d.d.d., J=14 Hz, 9 Hz and 7 Hz),
2.15 (1H, d.d.d., J=14 Hz, 9 Hz and 4 Hz),
2.97 (1H, d.d., J=13 Hz and 10 Hz),
3.03 (1H, d.d., J=16 Hz and 3 Hz),
3.21 (1H, d.d., J=13 Hz and 3 Hz),
3.57 (1H, d.d., J=16 Hz and 5 Hz),
4.13 (1H, m),
4.50 (1H, d.d., J=5 Hz and 3 Hz),
4.91 (1H, s),
5.02 (1H, d.d., J=9 Hz and 7 Hz),
5.84 (1H, s),
6.87 (1H, broad s)
6.96 (2H, m),
7.40 (3H, m);

(i) is soluble in water, and is sparingly soluble in acetone and ethanol, and is insoluble in hexane, ethyl acetate and chloroform;

(j) is positive in color reaction by each of Ninhydrin reaction and ferric chloride-potassium ferricyanide reaction, and is negative in color reaction by each of Molish's reaction and Dragendorff reagent or diacetyl reagent;

(k) is basic substance; and (l) has a characteristic $^{13}C$-Nuclear magnetic resonance absorption spectrum as shown in the following; δ(ppm) ($D_2O+DCl$): 174.0, 173.2, 168.6, 154.2, 152.8, 133.0, 132.9, 130.6, 127.9, 127.6, 127.2, 126.2, 120.3, 116.9, 116.4, 65.2, 64.4, 57.4, 55.0, 50.9, 44.9, 37.9, 30.4.

2. A process for the production of a compound FR-900451 or pharmaceutically acceptable salts thereof, which comprises culturing *Streptomyces griseorubiginosus* No. 43708 in a nutrient medium under aerobic conditions, and recovering a significant amount of FR-900451 or pharmaceutically acceptable salts thereof from the resultant cultured broth.

3. A pharmaceutical antibiotic composition comprising an antibiotically effective amount of the FR-900451 of claim 1 or pharmaceutically acceptable salts thereof in admixture with a pharmaceutically acceptable carrier.

4. A method for treating infectious diseases in human beings and animals which comprises administering to said human or animal an antibiotically effective amount of the compound FR-900451 of claim 1.

* * * * *